(12) United States Patent
Wang et al.

(10) Patent No.: US 8,248,613 B2
(45) Date of Patent: Aug. 21, 2012

(54) CAPTURING REFLECTED LIGHT FROM A SAMPLING SURFACE

(75) Inventors: Jiaping Wang, Beijing (CN); Moshe Benezra, Beijing (CN); Xin Tong, Beijing (CN); John Michael Snyder, Redmond, WA (US); Baining Guo, Beijing (CN)

(73) Assignee: Microsoft Corporation, Redmond, WA (US)

( * ) Notice: Subject to any disclaimer, the term of this patent is extended or adjusted under 35 U.S.C. 154(b) by 85 days.

(21) Appl. No.: 12/769,974

(22) Filed: Apr. 29, 2010

(65) Prior Publication Data

US 2011/0267619 A1 Nov. 3, 2011

(51) Int. Cl.
*G01N 21/55* (2006.01)
(52) U.S. Cl. .................................. 356/445; 356/446
(58) Field of Classification Search .......... 356/445–448, 356/237.2–237.5; 345/426–428, 419, 581–582
See application file for complete search history.

(56) References Cited

U.S. PATENT DOCUMENTS

| | | | |
|---|---|---|---|
| 6,765,573 B2 | 7/2004 | Kouadio | |
| 7,075,534 B2 | 7/2006 | Cole et al. | |
| 7,256,781 B2 | 8/2007 | Shioya | |
| 2006/0132486 A1 | 6/2006 | Kim et al. | |
| 2007/0216905 A1 | 9/2007 | Han et al. | |
| 2008/0309667 A1 | 12/2008 | Zhou et al. | |
| 2009/0006044 A1 | 1/2009 | Zhou et al. | |

OTHER PUBLICATIONS

Dana, Kristin J., "BRDF/BTF Measurement Device"—Published Date: 2001 http://citeseerx.ist.psu.edu/viewdoc/download?doi=10.1.1.77.3635&rep=rep1&type=pdf.
Dana; et al., "Device for convenient measurement of spatially varying bidirectional reflectance"—Published Date: Jan. 2004, vol. 21, No. 1/J. Opt. Soc. Am. A http://citeseerx.ist.psu.edu/viewdoc/download?doi=10.1.1.91.8806&rep=rep1&type=pdf.
Mattison; et al., "The Hand-Held Directional Reflectometer: An angular imaging device to measure BRDF and HDR in real-time"—Published Date: Jul. 1998 https://www.cis.rit.edu/~cnspci/references/mattison1998.pdf.
Mukaigawa; et al., "High-Speed Measurement of BRDF using an Ellipsoidal Mirror and a Projector"—Published Date: Jun. 22, 2007, http://citeseerx.ist.psu.edu/viewdoc/download?doi=10.1.1.99.546&rep=rep1&type=pdf.
Ben-Ezra; et al., "An LED-only BRDF Measurement Device"—Retrieved Date: Apr. 17, 2010 http://research.microsoft.com/en-us/um/people/jpwang/paper_stuffs/led_brdf_cvpr08.pdf.

*Primary Examiner* — Tri T Ton
(74) *Attorney, Agent, or Firm* — Microsoft Corporation

(57) ABSTRACT

A mechanism is disclosed for capturing reflected rays from a surface. A first and second lens aligned along a same optical center axis are configured so that a beam of light collimated parallel to the lens center axis directed to a first side, is converged toward the lens center axis on a second side. A first light beam source between the first and second lenses directs a light beam toward the first lens parallel to the optical center axis. Second light beam source(s) on the second side of the first lens, direct a light beam toward a focal plane of the first lens at a desired angle. An image capturing component, at the second side of the second lens, has an image capture surface directed toward the second lens to capture images of the light reflected from a sample capture surface at the focal plane of the first lens.

11 Claims, 11 Drawing Sheets

CAPTURING REFLECTED LIGHT FROM A SAMPLING SURFACE

BACKGROUND

Real-life objects can look different when viewed from different angles and when illuminated from different directions and/or angles. For example, when facing a low lying sun, a landscape may have a particularly different appearance than when viewing the same landscape at high noon. Painters and photographers often explore the appearance of trees, landscapes, people and urban areas under a variety of conditions, in order to accumulate knowledge about "how things look".

A reason that things look differently under different conditions can be related to how light is reflected from the surface of viewed objects. Light reflected in one direction may make an object appear different than when it is reflected in a different direction. Further, structural and optical properties of the surface of viewed objects, such as shadow-casting, multiple scattering, mutual shadowing, transmission, reflection, absorption and emission by surface elements, can also affect how an object appears. These characteristics of an object can be summarized by the reflectance on real-world objects, and the reflectance of a surface can be determined by a Bidirectional Reflectance Distribution Function (BRDF). Determining BRDFs, for example, can be useful for creating realistic computer-generated (CG) images.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

When one wishes to model a particular object, for example, as a computer-generated (CG) image (e.g., a piece of architecture, tree, furniture, etc.), they may attempt to determine Bidirectional Reflectance Distribution Functions (BRDFs) for that object. However, capturing BRDFs that have high resolution in both a spatial and angular domain is difficult. The surface of an object can often comprise a myriad of variations in surface elements, angles, and materials that absorb or reflect light, each of which adds to how that object appears in the real-world. Measuring BRDFs for various objects can generally take hours of measurement and processing, and use of large, specialized and expensive hardware rigs. As a result, not many materials have been measured for high resolutions BRDFs.

Systems are disclosed that provide for a relatively small, inexpensive, and easily manipulated apparatus that can capture images of light reflected from a sampled surface. Further, the disclosed systems can provide a variety of illumination positions and angles, thereby providing a more complete and accurate sequence of reflectance images from a sample, for example, when moved across the sample's surface. The image information captured by the systems described herein may be utilized to determine BRDFs for the surface of an object, for example, thereby providing for more accurate CG imagery, in a more efficient and cost effective manner than is conventionally known.

In one embodiment of an apparatus for capturing a field of reflected rays from a sample surface, at least a first and second lens are disposed along a same optical center axis, where the respective lenses are configured so that a beam of light, passing through the lens and collimated parallel to the lens center axis from a first side, is converged toward the lens center axis on a second side. Further, at least one first light beam source is between the first and second lenses, directing a light beam toward the first lens parallel to the optical center axis. Additionally, one or more second light beam sources are on the second side of the first lens, and they direct a light beam toward a focal plane of the first lens at a desired angle from the focal plane. An image capturing component at the second side of the second lens has an image capture surface directed toward the second lens, and it captures images of the light reflected from a sample capture surface at the focal plane of the first lens.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1A:
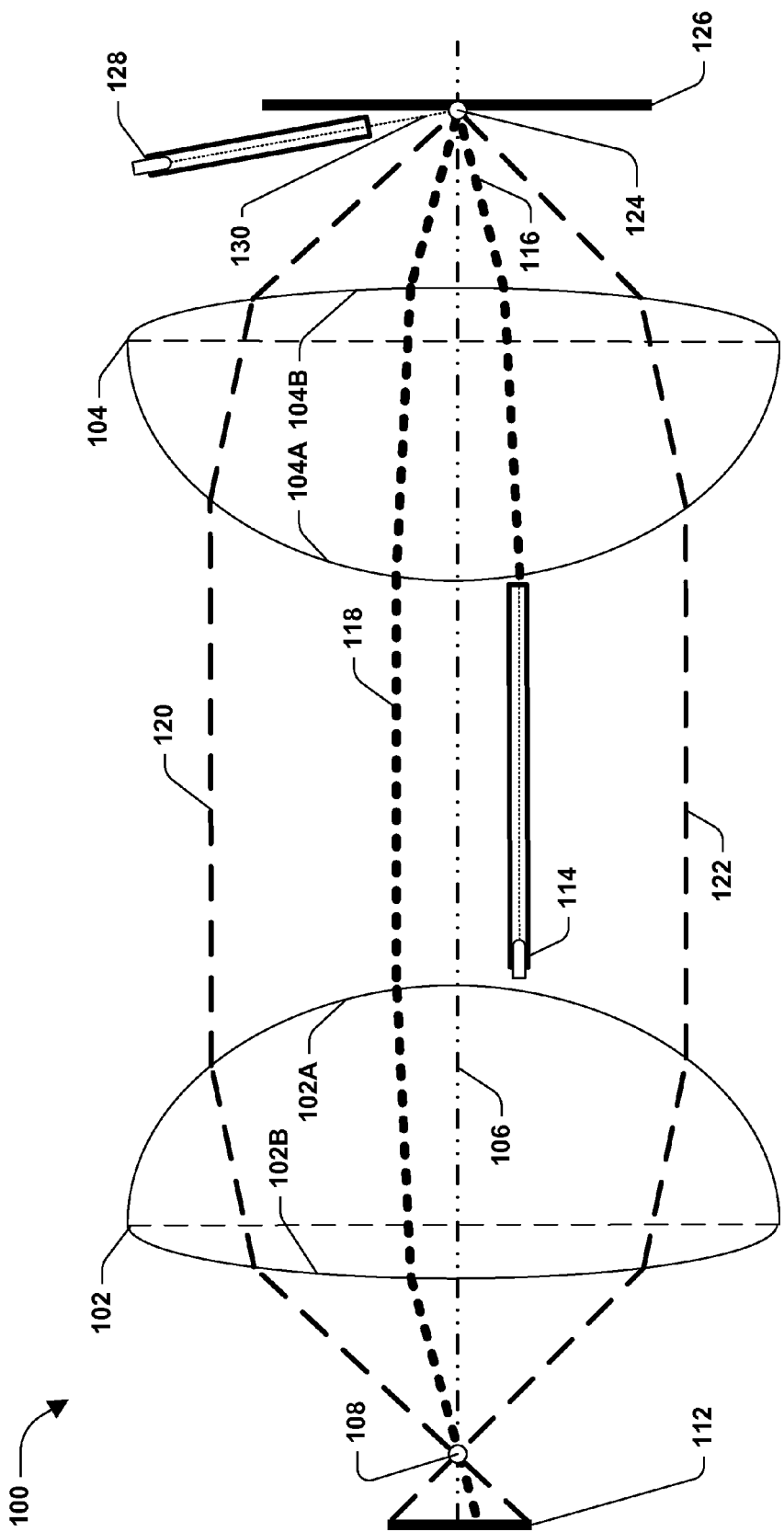
FIG. 1A is a component diagram illustrating an exemplary apparatus for capturing a hemispherical field of reflected rays from a sample surface.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

An apparatus may be devised that provides for capturing light reflected from a surface that is subjected to sampling. That is, for example, light directed toward a surface intended to be sampled can reflect from the sample surface and be captured for further processing. Light directed toward a surface can exhibit a variation of reflectance, which can also vary with different materials. Rich details of a material's surface may also change based on a position of the observer and a position of the light source. Surfaces of a variety of materials can be sampled, and light reflected from the sampling surface can be captured, for example, to create a computer-generated image of a surface which exhibits "real-world" visual characteristics of the sampled material.

FIG. 1 is a component diagram illustrating an exemplary apparatus 100 that can be used to capture a hemispherical field of reflected rays from a sample surface. A first lens 104 and second lens 102 are disposed such that they are aligned along a same optical center axis 106. Further, the lenses 102, 104 are disposed in manner that when a beam of light 116, which is collimated parallel to the lens's center axis 106, passes through a first side of the lens 104A the beam 116 is converged toward the lens's center axis 106, (e.g., at a front side of the lens). Additionally, the lenses 102, 104 are disposed in a manner where the first side 104A of the first lens 104 faces the first side 102A of the second lens 102.

A first light beam source 114 (or more than one) is disposed between the first lens 104 and the second lens 102. The first light beam source 114 directs a light beam 116 toward the first lens 104 parallel to the optical center axis 106. One or more second light beam sources 128 are disposed at the second side 104B of the first lens 104, where they direct a beam of light 130 toward a focal plane 124 (e.g., at a focal point) of the first lens 104 at a desired angle (e.g., chosen for a desired reflectance affect) from the focal plane 124.

One or more second light beam sources 128 are disposed on the second side 104B of the first lens 104. These one or more second light beam sources 128 respectively direct a light beam toward the focal plane 124 of the first lens 104 at a desired angle from the focal plane 124. That is, for example, a second light beam source can provide side lighting to a sample surface that is placed at the focal plane. The second light beam sources provide the side lighting at a desired angle, for example, to compliment the top lighting provided by the first light beam source(s). In this way, in this example, a plurality of reflections from the sample surface can be created from a plurality of positions, and at angles that may provide for desired resulting reflected light capture.

An image capturing component 112 is disposed on the second side 102B of the second lens 102. The image capturing component 112 has an image capture surface that faces the second lens 102, and captures images that are made up of light reflected 118, 120, 122 from a sample capture surface 126 at the focal plane 124 of the first lens 104. In one embodiment, the image capture surface of the image capturing component 112 can be disposed at a distance from a focal plane 108 (e.g., comprising a focal point) of the second lens 102, that provides a desired image focus for the reflected light 118, 120, 122.

In one embodiment, the first and second light beam sources 114, 128 are directed toward an intended sample surface 126, at a desired point on the surface. That is, for example, a plurality of second light beam sources 128 can be pointed toward the focal plane 124 of the first lens 104, and the first light beam source 114 can be positioned such that its beam of light 116 is converged at the focal plane of the first lens. In this way, in this example, the first light beam source 114 provides a top light source, and the second light beam sources 128 provide side light sources from a variety of positions. Therefore, light is reflected 118, 120, 122 from the sample surface 126 at a plurality of angles and positions, and that reflected light 118, 120, 122 can be directed back to the second lens 102, which converges the reflected light toward it's focal plane 108. The reflected light can then be captured as an image (or series of images) by the image capture component 112.

In one aspect, real-world materials exhibit rich and detailed reflectance variation, for example, due to textures, surface shapes, types of materials, and other structural and optical properties of the surface. These reflectances can be acquired to produce realistic computer-generated (CG) imagery of the materials. Objects look differently when viewed from different angles/locations and when light sources illuminate the objects from different angles/locations. Bidirectional reflectance distribution functions (BRDFs) give reflectance of a target surface as a function of illumination geometry and viewing geometry. That is, for example, a BRDF can help identify what an object's surface may look like based on the angle/location of illumination, and the angle/location of the point of view. In this aspect, light reflected from a surface at variety of locations and angles can be captured, and BRDFs may be determined for that material. In this way, in this example, the surface of an object may be more realistically modeled for CG imagery.

Figure 2:
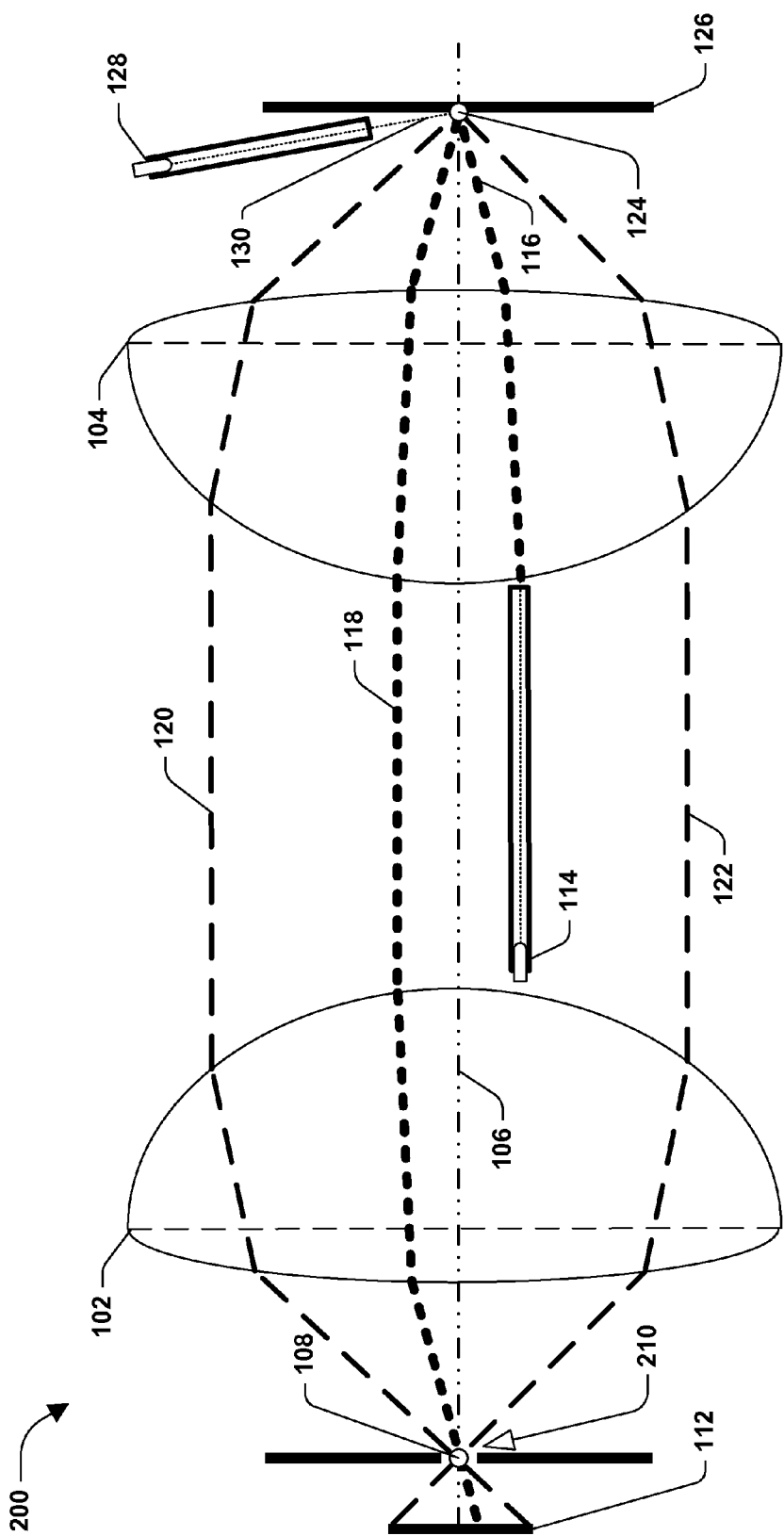
FIG. 2 is an example embodiment of an apparatus in accordance with the one or more systems disclosed herein.

In one embodiment, as illustrated in the exemplary embodiment 200 of FIG. 2, an aperture 210 is defined between the image capturing component 112 and the second lens 102, at the second side of the second lens. The center of the aperture 210 is aligned along the optical center axis 106, and a plane formed by the aperture 210 is aligned with the focal plane 108 of the second lens 102. In one embodiment, an aperture (e.g., 210) can provide for a desired cone angle for the reflected light (e.g., 118, 120, 122) at the focal plane (e.g., 108), thereby providing a desired image quality (e.g., focus, depth of field, etc.) at the image capture surface of the image capture device (e.g., 112).

An aperture can determine a cone angle of a plurality of reflected light rays that come to focus on an image plane, such as at the image capture surface. That is, for example, a small (e.g., narrow) aperture may provide for highly collimated light rays that result in a sharper image at the image plane on the image capture surface. Whereas as a larger aperture, which provides for a plurality of uncollimated rays, may result in sharpness for merely those rays having a focal length that matches the image plane on the image capture surface. In this way, for example, a size of the aperture may determine sharpness and other image qualities for the images of reflected light at the image capture surface.

Figure 3:
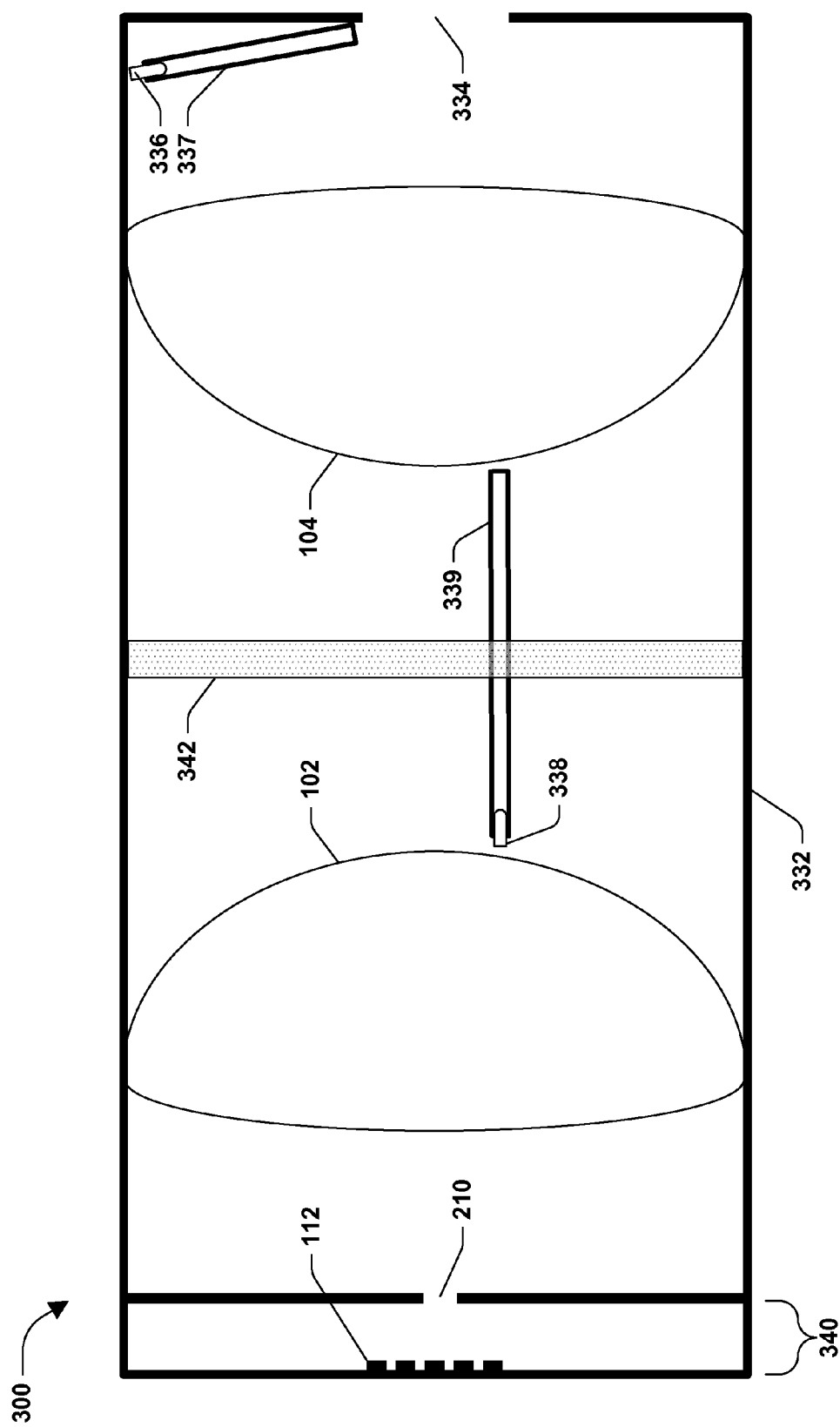
FIG. 3 is an example embodiment of an apparatus in accordance with the one or more systems disclosed herein.

In one embodiment, a device configured to detect reflected light, such as the apparatus of FIG. 1, for example, can comprise a casing, as illustrated by the exemplary embodiment 300 of FIG. 3. In this embodiment, the casing 332 can be configured to mitigate (e.g., prevent most if not all) light infiltration from outside the casing to inside the casing. That is, for example, the casing is designed to merely allow light from the first and second light beam sources to be directed toward the sample surface, and be reflected back to the image capture device, preventing extraneous light from affecting the sampling. In this way, in this example, light sources, angles and locations can be controlled for BRDF determination.

As illustrated in FIG. 3, the casing 332 can also be configured to provide for mounting the lenses 102, 104 and aperture 210 inside the casing in alignment along the optical center axis (e.g., 106 of FIG. 1). For example, the casing 332 may be cylindrical and have an inner diameter that is devised to merely fit an outer diameter of a cylindrical lens. In this way, for example, the lenses could be fastened in place at an appropriate location, such as using a type of adhesive, or a mechanical fixture or fastener, inside the casing.

Further, as an example, the aperture 210 may be formed by mounting an aperture ring inside the casing. In one embodiment, the aperture ring may be comprised of a same material, and formed together with the casing. In another embodiment, the aperture ring may be inserted into the casing and fastened therein at an appropriate location, such as coplanar with the focal plane of the second lens. It will be appreciated that the aperture is not limited to any particular size, and may be sized to fit a desired result for a particular application or sampling.

In one embodiment, as illustrated in the exemplary embodiment 300 of FIG. 3, the casing can comprise a sample capture opening 334 that is disposed at the second side of the first lens 104. The sample capture opening 334 can allow light from the first and second light sources 338, 336 to reach a sample capture surface that is placed adjacent to the sample capture opening 334. As an example, the example embodiment of an apparatus 300 can be held against a surface that is intended for sampling, with the sample capture opening 334 held adjacent to the sampling surface, which is coplanar with the focal plane of the first lens 104. In this way, in this example, light from the first light source 338 will focus on the sample surface, and light from the second light source(s) will illuminate the sample surface.

In the above example, light reflected from the sample surface is directed toward the first lens 104, and back toward the image capture surface 112 of the image capture component. In one embodiment, the casing 332 can comprise a mechanism for mounting at least the image capture surface 112 of the image capture component inside the casing. That is, for example, the casing 332 can be devised to provide a way to mount the image capture surface 112 at an appropriate distance 340 from the aperture 210, such that the image capture surface 112 is coplanar with a desired image plane for light reflected from the sample surface. In this way, in this example, at least the image capture surface 112 is mounted inside the casing 332 so that merely reflected light from the sample surface reaches its surface, and not light from outside the casing 332.

It will be appreciated that the systems described herein are not limited to any particular embodiment for mounting the image capture component. For example, merely the image capture surface, such as a complementary metal-oxide-semiconductor (CMOS) sensor, of the image capture component, such as a digital camera, can be located inside the casing in order to capture the reflected light. However, in another example, an entire camera, or portions thereof, may be disposed inside the casing such that the reflected light reaches the sensor of the camera at the desired image plane.

Figure 6:
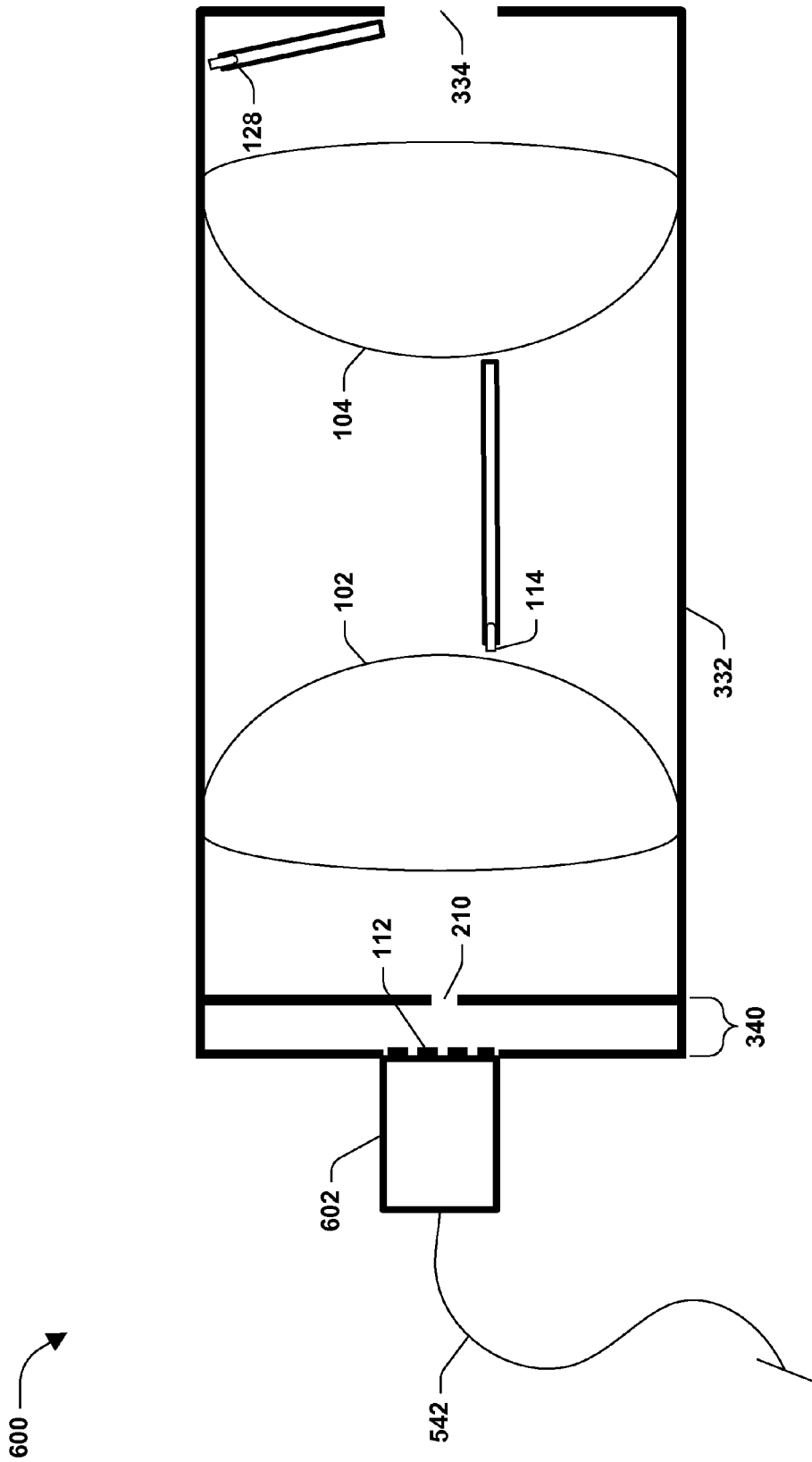
FIG. 6 is an example embodiment of a device in accordance with the one or more systems disclosed herein.
Figure 7A:
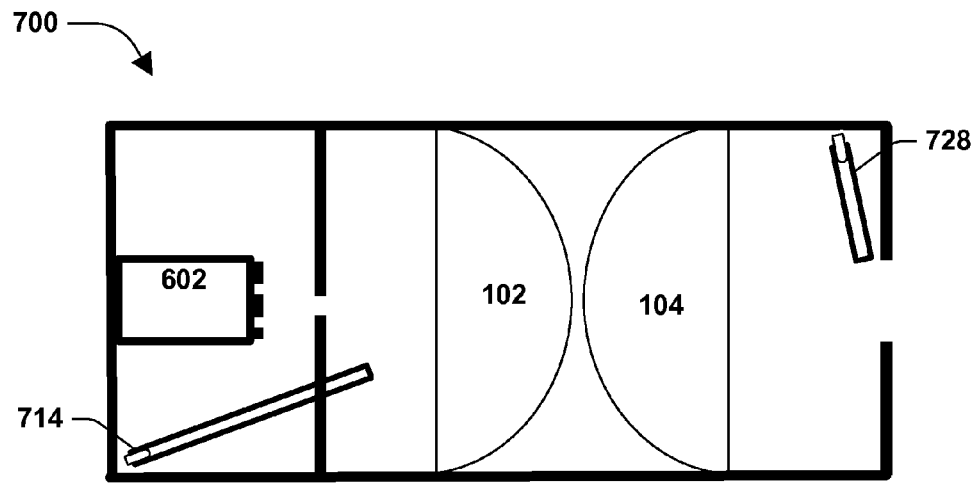
FIGS. 7A-C are example embodiments illustrating a variety of arrangements of components in an apparatus in accordance with the one or more systems described herein.

FIG. 6 illustrates one exemplary embodiment 600, where the image capture device 602 is comprised outside of the casing 332, and merely the image capture surface 112 is disposed inside the casing 332 at a distance 340 from the aperture 210 that provides for capturing the reflected light at a desired image plane, for example. FIG. 7A illustrates another example embodiment 700, where the image capture device 602 is disposed entirely inside the casing, such that the reflected light is captured at a desired image plane. In another embodiment, the image capture surface may comprise a lens that focuses the reflected light to an image light sensor, such as a CMOS sensor, in a camera, for example.

In one embodiment, the casing 332 can comprise a mechanism for mounting the light beam sources. As illustrated in the exemplary embodiment 300 of FIG. 3, a light beam source may be comprised of a light source 338, 336 and a light tube 339, 337, which can direct the light from the light source as a beam to a desired location. For example, the light source 338, 336 may comprise a light emitting diode (LED), which typically emits light in a plurality of directions. The light source can be disposed in a light tube 339, 337 such that merely a light beam is emitted at a desired direction. The light beam source (e.g., comprised of the light source 338, 336 and the light tube 339, 337) can be mounted by a mechanism comprised by the casing.

In one embodiment, the mechanism for mounting the first light beam source 338, 339 may be comprised of an optically clear casing insert 342 that anchors the first light beam source 338, 339 at a desired position between the first and second lenses 104, 102. As an example, an acrylic disk (e.g., 342) may be inserted inside the casing, in which can be mounted the first light beam source at a desired position. In this example, the acrylic disk (or some other optically clear polymer, glass, or material that does not alter an angle of light passing through it at a perpendicular direction) may comprise an opening in which the light tube (e.g., 339) of the light beam source can be mounted.

In one embodiment, the first light beam source is disposed at a distance from the optical center axis that provides for light from the first light beam source to reach the lens axis at a desired angle of bias from the optical center axis. That is, for example, with reference to FIG. 1, varying the distance between the first light beam source 114 from the optical center axis 106 can vary the angle at which the light beam 116 from the first light beam source intersects the optical center axis 106 at the focal plane 124. As illustrated in FIG. 1, a light beam directed toward the first lens 104 from position 122 has a larger angle of bias from the optical center axis 106 than the light beam directed from the position 118. The first light beam source may be mounted at such a distance that provides for a desired result, such as for a desired type of sampling. Further, a plurality of first light beam sources may be mounted at a same or varied distances from the optical center, for example, in order to provide top lighting for the sample surface from a variety of angles.

Figure 4A:
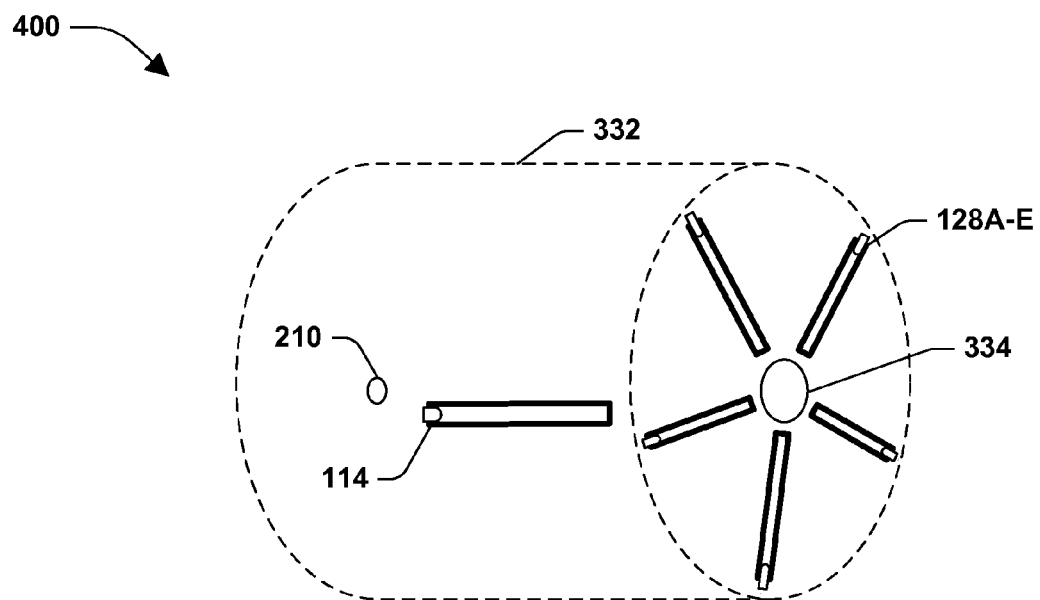
FIGS. 4A-D are example embodiments illustrating arrangements of light beam sources in an apparatus in accordance with the one or more systems described herein.
Figure 4B:
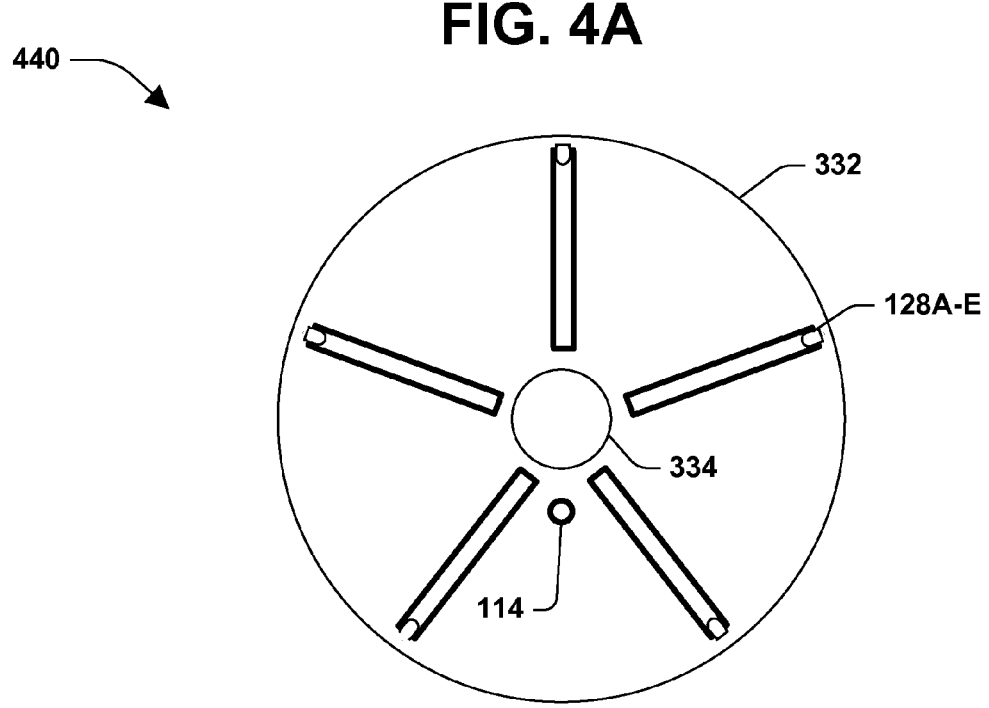

In one embodiment, the mechanism for mounting the one or more second light beam sources can provide for mounting the second light beam source entirely inside the casing, such as illustrated in the example embodiments 400 of FIG. 4A and 440 of FIG. 4B. That is, for example, five second light beam sources 128A-E can be arranged relatively equidistant from each other around the sample capture opening 334, mounted in such a way as to provide for the second light beam sources 128 to direct their light beams toward the sample capture opening 334 (e.g., to provide a plurality of lighting perspectives).

Figure 4C:
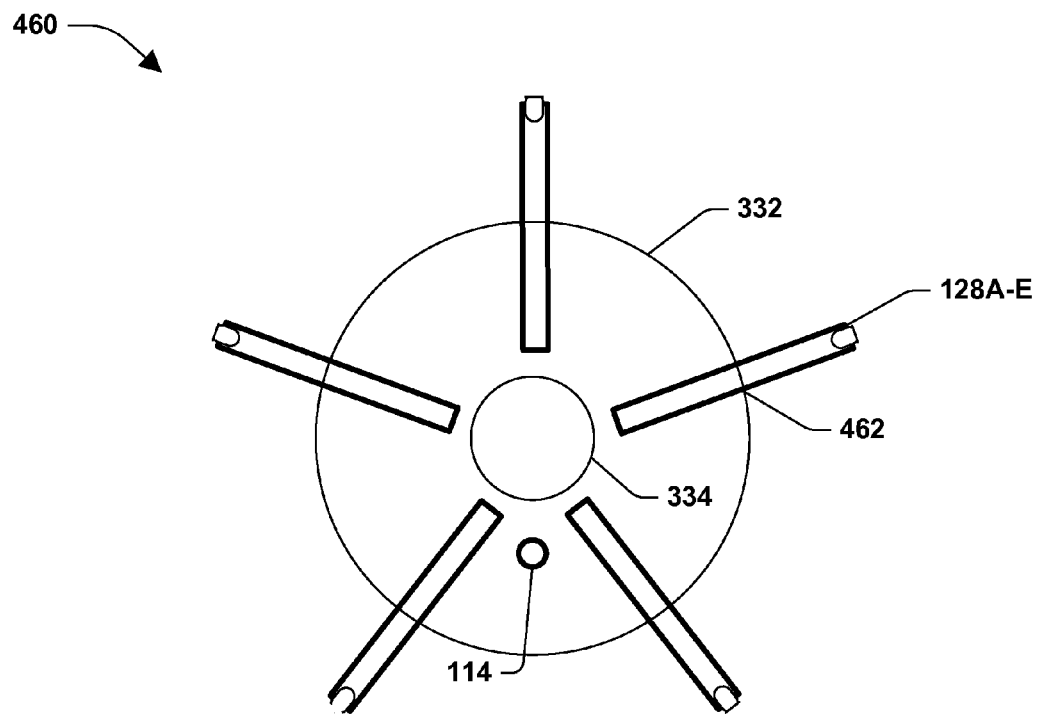

In another embodiment, the mechanism for mounting the one or more second light beam sources 128 can provide for mounting the second light beam source 128 so in a way that merely provides for the light beam to be directed toward the sample capture surface placed adjacent to the sample capture opening 334. That is, for example, the mounting mechanism may provide for mounting the second light beam source (e.g., 128A-E) completely or partially outside the casing 332, in a way that allows the light to still reach the sample capture opening 334. One example of this embodiment is illustrated in FIG. 4C, where the casing 332 comprises openings 462 that provide for mounting the five second light beam sources 128A-E, so that the light beams are directed toward the sample capture opening 334.

Figure 4D:
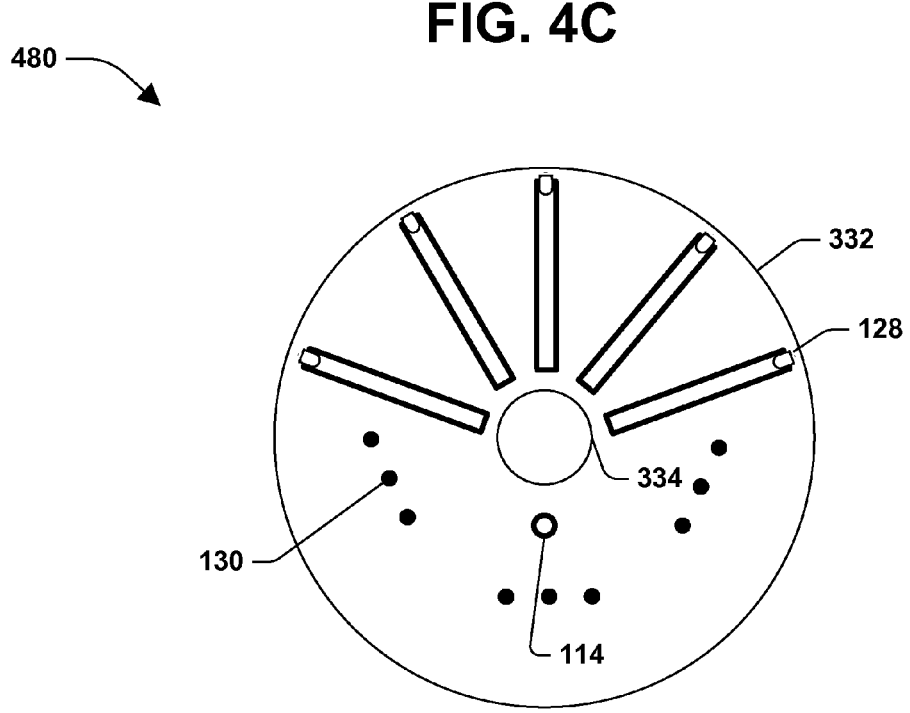

It will be appreciated that the number of first and second light beam sources are not limited to the embodiments described herein. As an example, as illustrated by the exemplary embodiment 480 of FIG. 4D, a plurality of second light beam sources 128, 130 may be disposed around the sample capture opening 334. In one embodiment, a size of the sample capture opening, which may be dictated by a type and size of a sampled surface, may necessitate additional second light beam sources, and/or first light beam sources 114.

Figure 8A:
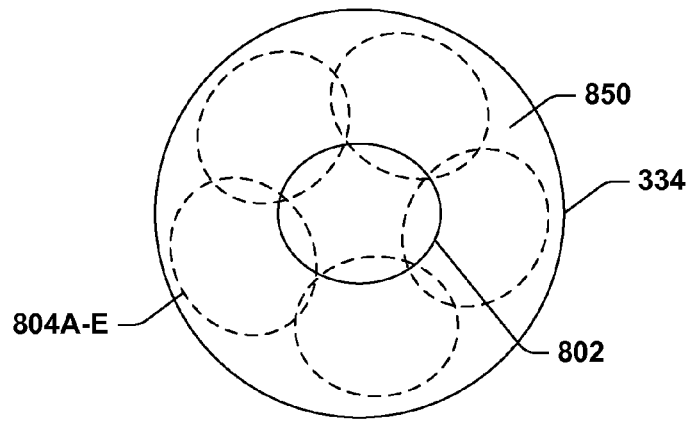
FIGS. 8A-B are example embodiments illustrating concepts in accordance with the one or more systems disclosed herein.
Figure 8B:
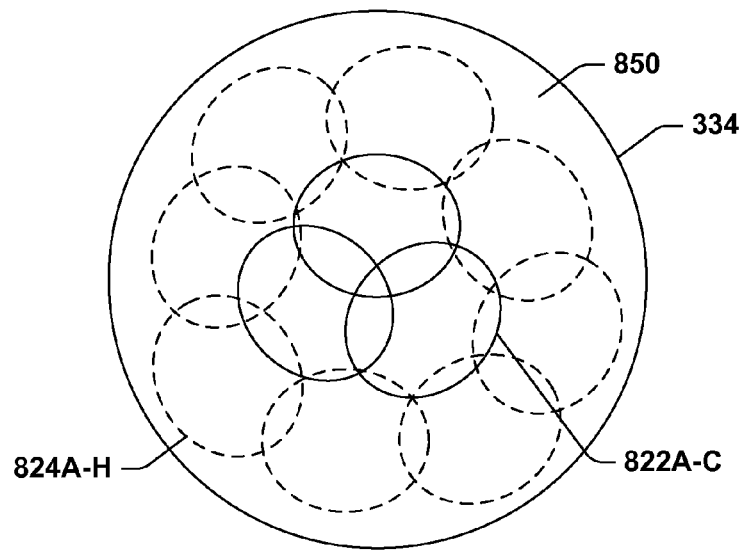

As illustrated in the exemplary embodiment 800 of FIG. 8A, five second light beam sources may provide five illuminated areas 804A-E on a sample capture surface 850 in the sample capture opening 324, while the first light beam source provides a single illuminated area 802 on the sample capture surface 850 in the sample capture opening 324. In this way, for example, a significant portion of the sample surface 850 can be illuminated during sampling. In another embodiment, as illustrated in 820 of FIG. 8B, eight second light beam sources can provide for eight illuminated areas 804A-H on a sample capture surface 850 in the sample capture opening 324. Further, in this embodiment, three first light beam sources can provide three illuminated areas 802A-C on a sample capture surface 850 in the sample capture opening 324.

Figure 7B:
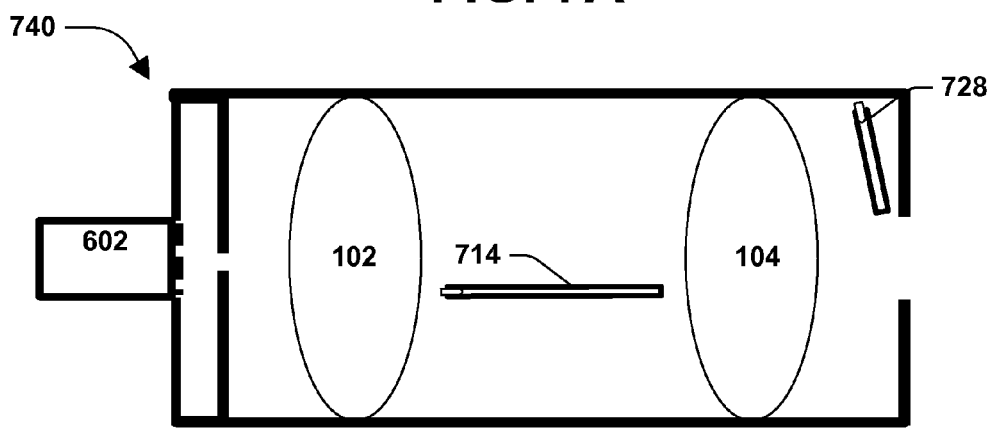

In one embodiment, the respective lenses may comprise plano-convex condenser lenses, where the first side of each lens is a non-focal-point side and the second side is a focal-point side. An example of plano-convex lenses is illustrated in the exemplary embodiment 700 of FIG. 7. The lenses 102 and 104 respectively comprise a flat side (plano) and a side that curves outward (convex). In this example, the focal point side is typically the flat side of the lens, where light beams are focused toward the lens's central axis, and the non-focal point side is typically the convex side, where light beams are collimated parallel to the lens's central axis.

It will be appreciated that the lenses and lens arrangements are not limited to those embodiments described above. As an example, as illustrated by the exemplary embodiment 700 of FIG. 7A, 740 of FIG. 7B, and 780 of FIG. 7C, the lens may be different shapes and can be arranged in different configurations. As an example, in FIG. 7A, the respective lenses 102, 104 are plano-convex and are arranged such that the convex sides face each other. In this example 700, the first light beam source 714 is disposed on the plano side of lens 102, angled such that when then light beam from this light passes through lens 102, it is collimated to the center axis before reaching lens 104. At lens 104, the light beam is converged toward the focal plane of lens 104, for example, at the sample surface.

In the example 740, the lenses 102, 104 are bi-convex. This arrangement of lenses can also provide for light beams to be focuses toward the center axis at either side of the lens arrangement. In this way, light from the first light beam source 714 is converged toward the axis of lens 104, for example, at a sample surface. The resulting reflected light is collimated by lens 104 parallel to the center axis, and at lens 102, it is converged towards a focal plane, for example, and the resulting image can be captured at the image plane by the image capture component 602.

Figure 7C:
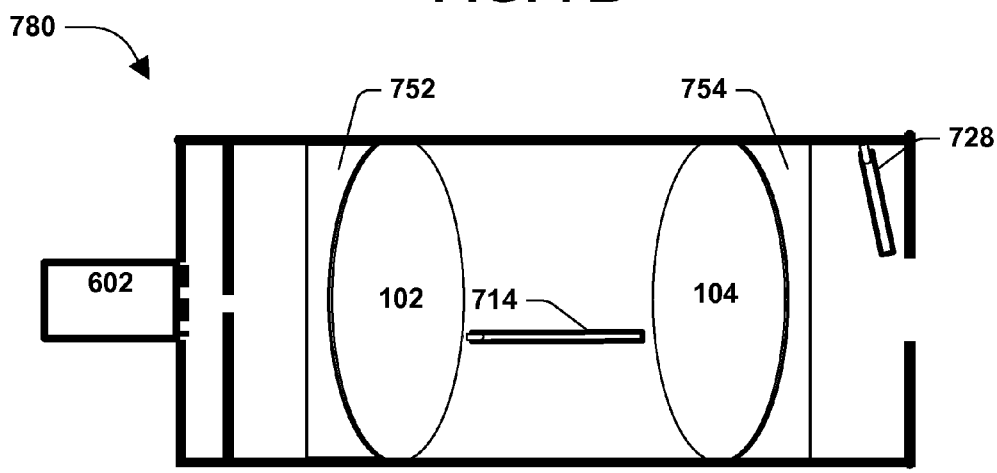

Further, the apparatus is not limited to merely two lenses. For example, as illustrated in FIG. 7C, respective bi-convex lenses 102 and 104 are disposed adjacent to two plano-concave lenses 752, 754. As described above, light from the first light beam source 714 is converged toward the axis of the combined lenses 104 and 754, for example, at the sample surface. The resulting reflected light is collimated by the combined lenses 104 and 754 parallel to the center axis, and at the combined lenses 102 and 752, the reflected light is converged towards the focal plane.

Figure 5:
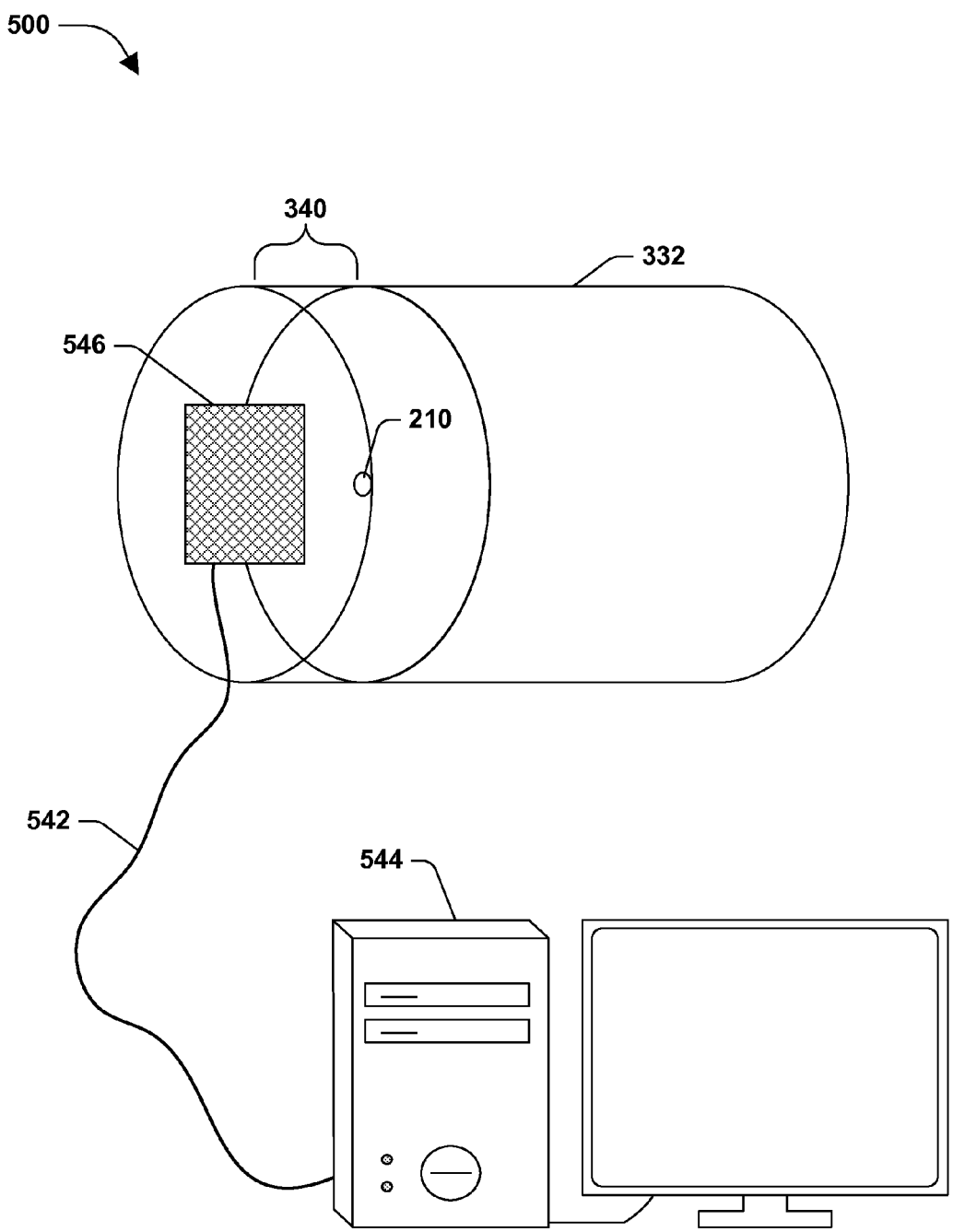
FIG. 5 is an example embodiment illustrating arrangements of image capture devices in accordance with the one or more systems described herein.

In one embodiment, the image capture component may have a computing device connector that allows for images captured by the image capture device to be provided to a computing device. FIG. 5 illustrates an exemplary embodiment 500 of how the apparatus may be connected to a computing device. The image capture component 546, having its image capture surface disposed inside the casing 332, is connected 542 to a computing device 544. The connection between the image capture component 546 and the computing device is not limited to any particular embodiment. For example, common connections utilized may comprise an IEEE 1394 interface (e.g., firewire), a USB connection, or a wireless connection (e.g., radio frequency, such as wifi or Bluetooth). In this way, for example, the captured images can be processed by the computing devices, such as to compute BRFDs.

Figure 1B:
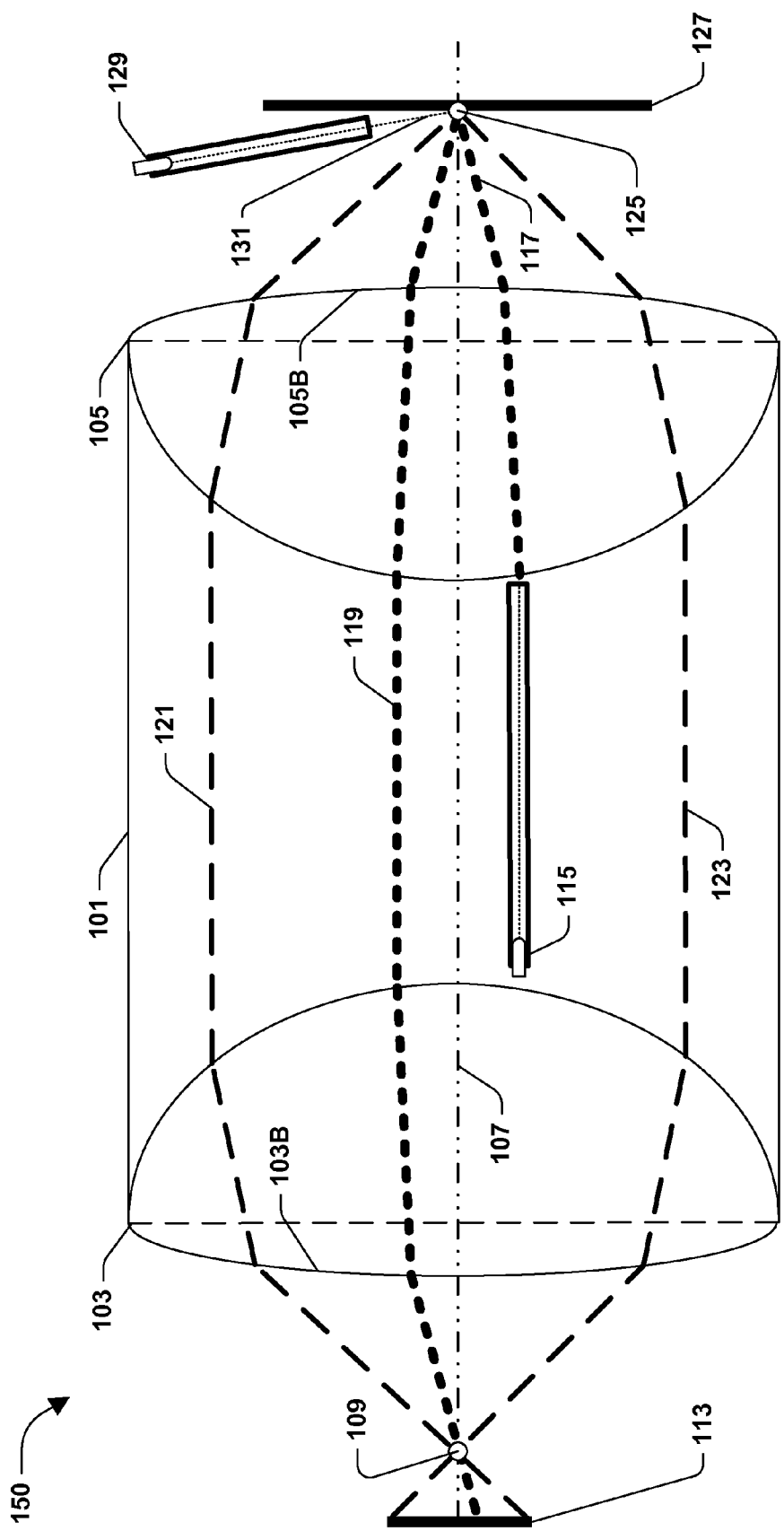
FIG. 1B is component diagram illustrating an exemplary system for capturing sparse light direction measurements from reflected rays from a sample surface.

As an alternate embodiment, FIG. 1B illustrates an example system 150 for capturing sparse light direction measurements from reflected rays from a sample surface. A compound lens 101 comprising at least two lenses 103 and 105, where the compound lens has a focal plane 125, 109 at both a first 105B and second 103B end. A first light source 115 directs light 117 toward the focal plane 125 at the first end 105B, where a light beam 117 from the first light source 115 has an angle of bias from an optical center axis 107 of the compound lens 101 of greater than or equal to zero degrees and less than or equal to forty-five degrees.

In this embodiment 150, one or more second light sources 129 direct light 131 toward the focal plane 125 at the first end 105B, where a light beam 131 from the second light source 129 has an angle of bias from the focal plane 125 of less than or equal to forty-five degrees and greater than or equal to zero degrees. An image capture device 113 is disposed at the second end 103B to capture light reflected from the focal plane 125 of the first end 105B at an image plane of the second end 103B.

In one embodiment, the image plane of the second end, such as disposed coplanar to an image capture surface of the image capture device 113, and the second end 103B of the compound lens 101 define an aperture (e.g., as illustrated by 210 of FIG. 2) between them, where the aperture is coplanar with the focal plane 109 of the second end 103B, with its center aligned along the optical center axis 107. As described above, this aperture can provide a desired cone angle for the reflected light, such as from a sample surface disposed coplanar to the focal plane 125 at the first end 105B.

In one embodiment, the exemplary system described above can be disposed in a casing that mitigates light infiltration from outside to inside the casing, such as illustrated by 332 of FIG. 3. In this embodiment, with reference to FIG. 1B and FIG. 3, the casing can comprise a sampling window (e.g., 334) that is disposed at the first end 105B adjacent to the focal plane 125 of the first end 105B. The sampling window can provide for light from the first 115 and second 129 light sources to reach a sample surface that may be placed adjacent to the sampling window, such as at the focal plane 125.

Further, in this embodiment, the casing can comprise a mechanism for mounting an image capture surface (e.g., 112 of FIG. 3) of the image capture device 113 at the image plane of the second end 103B. In this way, as described above, at least the image capture surface is disposed inside the casing, thereby allowing merely light reflected from the sample surface to be captures by the image capture device, for example, and not extraneous light.

In one embodiment, with reference to FIG. 1B and FIG. 3, the exemplary system can comprise a first light source mounting mechanism (e.g., 342) that provides for mounting the first light source 115 so that light from the first light source 115 remains inside the casing (e.g., 332) until light from the first light source 115 reaches the sampling window (e.g., 334).

That is, the mounting mechanism allows the first light source to direct light toward the first end 105B of the compound lens 101, where it is converged toward the focal plane 125 of the first end 105B, for example, at which may be placed a sample surface.

Further, in this embodiment, the exemplary system can comprise a second light source mounting mechanism that provides for mounting the second light source 129 so that light from the second light source 129 remains inside the casing (e.g., 332) until light from the second light source 129 reaches the sampling window (e.g., 334). That is, the mounting mechanism provides for the one or more second light sources, for example, to be mounted around the sampling window, with their light beams directed toward the focal plane 125 of the second end 105B.

In one embodiment, the first light source can be disposed between the first 105 and second 103 lens inside the compound lens 101. In this embodiment, light 117 from the first light source 115 is directed toward the sampling window (e.g., 334), and the first and second lens are disposed in a manner inside the compound lens 101 that merely accommodates the first light source 115. In this embodiment, the first light source 115 is placed between the lenses of the compound lens, with its beam aiming toward the first end 105B, for example, to provide top light illumination to a sample surface at the focal plane 125. In this embodiment, for example, an optically clear disk (e.g., 342) may be employed to mount the first light source 115 between the lenses in the compound lens 101.

In one embodiment, with reference to FIGS. 1B and 5, the image capture device 113 has a mechanism (e.g., 542) that provides for images captured by the image capture device to be provided to a computing device (e.g., 544). In this embodiment, the computing device can be configured to compute microfacet bidirectional reflectance distribution functions (BRDFs). That is, for example, a plurality of images of reflected light may be collected by the image capture device 113 as the casing comprising the exemplary system is moved over a sample surface. In this way, in this example, the plurality of images may be used by the computing device to calculate BRDFs for the sample surface (e.g., to create CG images of the surface).

In one embodiment, the exemplary system, such as 150 of FIG. 1B, may comprise a mechanism for adjusting particular elements of the system. A mechanism may be provided that adjusts the aperture (e.g., 210 of FIG. 2), such as to sharpen the image at the image plane on the image capture surface. Further, a mechanism may be provided that adjusts a distance of the aperture from the image capture surface, such as to provide for additional focus and image enhancements. Additionally, a mechanism may be provided that adjusts a distance between the first and second lens, such as to adjust the focal plane at either or both of the first and second ends of the compound lens.

In another embodiment, other adjustment mechanisms may be provided. A mechanism may be provided that adjusts a color of the respective lights sources, for example, in order to correct for sample surface conditions. A mechanism may be provided that adjusts a brightness of respective light sources, such as to enhance or adjust desired sampling conditions.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Figure 9:
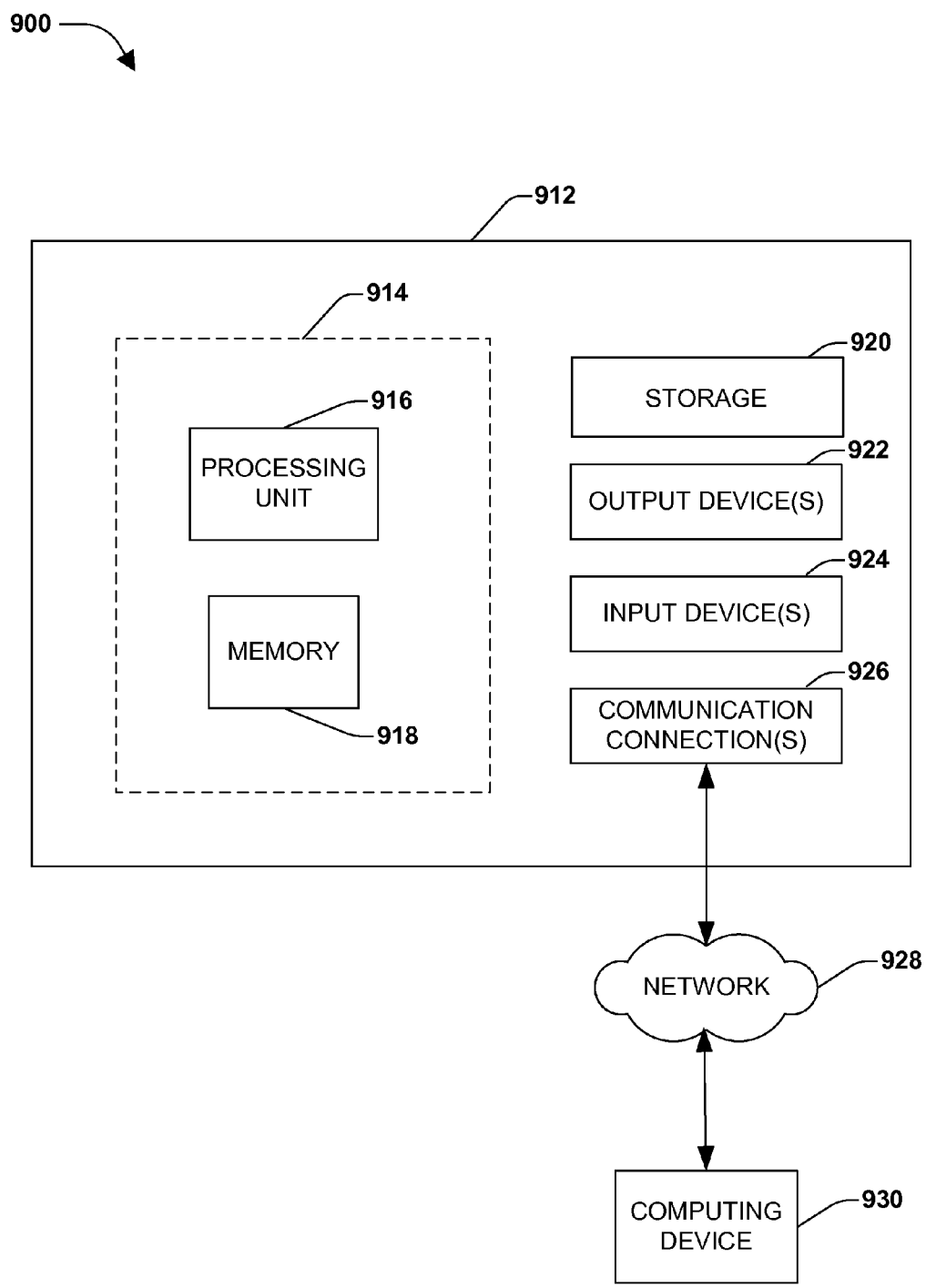
FIG. 9 illustrates an exemplary computing environment wherein one or more of the provisions set forth herein may be implemented.

FIG. 9 and the following discussion provide a brief, general description of a suitable computing environment to implement embodiments of one or more of the provisions set forth herein. The operating environment of FIG. 9 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 9 illustrates an example of a system 910 comprising a computing device 912 configured to implement one or more embodiments provided herein. In one configuration, computing device 912 includes at least one processing unit 916 and memory 918. Depending on the exact configuration and type of computing device, memory 918 may be volatile (such as RAM, for example), non-volatile (such as ROM, flash memory, etc., for example) or some combination of the two. This configuration is illustrated in FIG. 9 by dashed line 914.

In other embodiments, device 912 may include additional features and/or functionality. For example, device 912 may also include additional storage (e.g., removable and/or non-removable) including, but not limited to, magnetic storage, optical storage, and the like. Such additional storage is illustrated in FIG. 9 by storage 920. In one embodiment, computer readable instructions to implement one or more embodiments provided herein may be in storage 920. Storage 920 may also store other computer readable instructions to implement an operating system, an application program, and the like. Computer readable instructions may be loaded in memory 918 for execution by processing unit 916, for example.

The term "computer readable media" as used herein includes computer storage media. Computer storage media includes volatile and nonvolatile, removable and non-removable media implemented in any method or technology for storage of information such as computer readable instructions or other data. Memory 918 and storage 920 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 912. Any such computer storage media may be part of device 912.

Device 912 may also include communication connection(s) 926 that allows device 912 to communicate with other devices. Communication connection(s) 926 may include, but is not limited to, a modem, a Network Interface Card (NIC), an integrated network interface, a radio frequency transmitter/receiver, an infrared port, a USB connection, or other interfaces for connecting computing device 912 to other computing devices. Communication connection(s) 926 may include a wired connection or a wireless connection. Communication connection(s) 926 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 912 may include input device(s) 924 such as keyboard, mouse, pen, voice input device, touch input device, infrared cameras, video input devices, and/or any other input device. Output device(s) 922 such as one or more displays, speakers, printers, and/or any other output device may also be included in device 912. Input device(s) 924 and output device(s) 922 may be connected to device 912 via a wired connection, wireless connection, or any combination thereof. In one embodiment, an input device or an output device from another computing device may be used as input device(s) 924 or output device(s) 922 for computing device 912.

Components of computing device 912 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 912 may be interconnected by a network. For example, memory 918 may be comprised of multiple physical memory units located in different physical locations interconnected by a network.

Those skilled in the art will realize that storage devices utilized to store computer readable instructions may be distributed across a network. For example, a computing device 930 accessible via network 928 may store computer readable instructions to implement one or more embodiments provided herein. Computing device 912 may access computing device 930 and download a part or all of the computer readable instructions for execution. Alternatively, computing device 912 may download pieces of the computer readable instructions, as needed, or some instructions may be executed at computing device 912 and some at computing device 930.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An apparatus for capturing a hemispherical field of reflected rays from a sample surface, comprising:
    at least a first and second lens, respective lenses configured such that a beam of light, passing through a lens and collimated parallel to a lens center axis from a first side, is converged toward the lens center axis on a second side, respective lenses aligned along an optical center axis, where a first side of the first lens faces a first side of the second lens;

a first light beam source disposed between the first and second lenses, configured to direct a first light beam toward the first lens parallel to the optical center axis;

one or more second light beam sources disposed on a second side of the first lens, respectively configured to direct a second light beam toward a focal plane of the first lens at a desired angle from the focal plane; and an image capturing component disposed on a second side of the second lens, having an image capture surface directed toward the second lens, and configured to capture images comprised of light reflected from a sample capture surface at the focal plane of the first lens.

2. The apparatus of claim 1, the image capturing component and the second lens defining an aperture therebetween disposed at the second side of the second lens and having a center aligned along the optical center axis, and a plane formed by the aperture aligned with a focal plane of the second lens.

3. The apparatus of claim 1, comprising a casing configured to:
mitigate light infiltration from outside the casing to inside the casing; and
provide for mounting the first and second lenses and an aperture inside the casing in alignment along the optical center axis.

4. The apparatus of claim 3, the casing comprising a sample capture opening disposed at the second side of the first lens, and configured to allow light from the first and second light beam sources reach the sample capture surface placed adjacent to the sample capture opening.

5. The apparatus of claim 3, the casing comprising a mechanism for mounting at least the image capture surface of the image capturing component inside the casing.

6. The apparatus of claim 3, the casing comprising a mechanism for mounting the first light beam source and at least some of the one or more second light beam sources.

7. The apparatus of claim 6, the mechanism for mounting comprising an optically clear casing insert configured to anchor the first light beam source at a desired position between the first and second lenses.

8. The apparatus of claim 6, the mechanism for mounting configured to provide for:
mounting at least some of the one or more second light beam sources entirely inside the casing; or
mounting at least some of the one or more second light beam sources so that the second light beam is directed toward the sample capture surface placed adjacent to the sample capture opening.

9. The apparatus of claim 1, the first and second lenses comprising plano-convex condenser lenses.

10. The apparatus of claim 1, the first light beam source disposed at a distance from the optical center axis that provides for light from the first light beam source to reach the lens center axis at a desired angle of bias from the optical center axis.

11. The apparatus of claim 1, the image capture component comprising a computing device connector configured to communicate images captured by the image capturing component to a computing device.

* * * * *